(12) United States Patent  
Gibbs

(10) Patent No.: US 8,895,265 B2  
(45) Date of Patent: Nov. 25, 2014

(54) MULTISTAGE FRACTIONATION PROCESS FOR RECALCITRANT $C_5$ OLIGOSACCHARIDES

(75) Inventor: Phillip R. Gibbs, Atlanta, GA (US)

(73) Assignee: Renmatix, Inc., King of Prussia, PA (US)

( * ) Notice: Subject to any disclaimer, the term of this patent is extended or adjusted under 35 U.S.C. 154(b) by 0 days.

(21) Appl. No.: 13/464,424

(22) Filed: May 4, 2012

(65) Prior Publication Data

US 2012/0282656 A1 Nov. 8, 2012

Related U.S. Application Data

(60) Provisional application No. 61/482,400, filed on May 4, 2011.

(51) Int. Cl.
| | |
|---|---|
| C12P 7/16 | (2006.01) |
| C12P 7/10 | (2006.01) |
| C12P 7/06 | (2006.01) |
| C12P 19/04 | (2006.01) |
| C12P 19/12 | (2006.01) |
| C12P 19/02 | (2006.01) |
| C12P 19/00 | (2006.01) |
| C07H 1/08 | (2006.01) |
| C07H 3/06 | (2006.01) |
| C08H 8/00 | (2010.01) |

(52) U.S. Cl.
CPC .. C07H 1/08 (2013.01); C07H 3/06 (2013.01); C08H 8/00 (2013.01); C12P 19/02 (2013.01); C12P 7/10 (2013.01); C12P 7/16 (2013.01); C12P 2201/00 (2013.01); C12P 2203/00 (2013.01); Y02E 50/10 (2013.01); Y02E 50/16 (2013.01)
USPC .............................................. 435/72; 127/36

(58) Field of Classification Search
CPC .......... C12P 19/04; C12P 19/12; C12P 19/02; C12P 7/06; C12P 7/10; C12P 19/00; C12P 7/16

See application file for complete search history.

(56) References Cited

U.S. PATENT DOCUMENTS

| | | | |
|---|---|---|---|
| 5,424,417 A | | 6/1995 | Torget et al. |
| 5,705,369 A | | 1/1998 | Torget et al. |
| 5,932,452 A | * | 8/1999 | Mustranta et al. ............ 435/105 |
| 6,022,419 A | | 2/2000 | Torget et al. |
| 6,228,177 B1 | | 5/2001 | Torget |
| 8,057,639 B2 | | 11/2011 | Pschorn et al. |
| 2004/0231661 A1 | | 11/2004 | Griffin et al. |
| 2005/0065336 A1 | | 3/2005 | Karstens |
| 2006/0091577 A1 | | 5/2006 | Shen et al. |
| 2010/0043782 A1 | | 2/2010 | Kilambi |
| 2010/0069626 A1 | | 3/2010 | Kilambi |
| 2010/0170504 A1 | | 7/2010 | Zhang |
| 2010/0203605 A1 | | 8/2010 | Kim et al. |
| 2010/0233771 A1 | | 9/2010 | McDonald et al. |
| 2012/0282655 A1 | | 11/2012 | Gibbs |

FOREIGN PATENT DOCUMENTS

| | | |
|---|---|---|
| CA | 1010859 | 5/1977 |
| CN | 1680415 | 10/2005 |
| CN | 1931866 | 3/2007 |
| CN | 101787398 | 7/2010 |
| CZ | 225851 | 3/1984 |
| CZ | 248106 | 1/1987 |
| EP | 814676 | 1/1998 |
| EP | 1304412 | 4/2003 |
| FR | 2580669 | 10/1986 |
| GB | 1569138 | 6/1980 |
| JP | 04197192 | 7/1992 |
| JP | 2006255676 | 9/2006 |
| JP | 2009077697 A * | 4/2009 |
| JP | 2009189291 | 8/2009 |
| JP | 2010042604 | 2/2010 |
| KR | 20090039470 | 4/2009 |
| WO | 9817727 | 4/1998 |
| WO | 9923260 | 5/1999 |
| WO | 0061276 | 10/2000 |
| WO | 0132715 | 5/2001 |
| WO | 2004013409 | 2/2004 |
| WO | 2006128304 | 12/2006 |
| WO | 2009060126 | 5/2009 |
| WO | 2010045576 | 4/2010 |
| WO | 2010046532 | 4/2010 |
| WO | 2010071805 | 6/2010 |
| WO | 2010102060 | 9/2010 |
| WO | 2011091044 | 7/2011 |
| WO | 2012151526 | 11/2012 |

OTHER PUBLICATIONS

Torget "Optimization of Reverse-Flow, Two-Temperature, Dilute-Acid Pretreatment to Enhance Biomass Conversion to Ethanol" Applied Biochemistry and Biotechnology vol. 57/58 1996, 85-101.*
Kim "Plug-Flow Reactor for Continuous Hydrolysis of Glucans and Xylans from pretreated Corn Fiber" Energy &Fuels, 2005, 2189-2200.*
Merriam-Webster ("Suspension" Obtained from www.merriam-webster.com/dictionary/suspension, accessed on Dec. 16, 2013).*
Tian et al. "Yeast strains for ethanol production from lignocellulosic hydrosylates during in situ detoxification" Biotechnology Advances (2009) 27, 656-660.*
Baek et al., "Optimization of the pretreatment of rice straw hemicellulosic hydrolyzates for microbial production of xylitol", Biotechnology and Bioprocess Engineering, 12(4), 2007, 404-9.

(Continued)

Primary Examiner — Jon P Weber
Assistant Examiner — Charles Zoltan Constantine
(74) Attorney, Agent, or Firm — Travis B. Gasa; Ballard Spahr LLP

(57) ABSTRACT

Methods are disclosed for increasing the level of $C_5$ monosaccharides produced from lignocellulosic biomass using a multistage fractionation process to handle recalcitrant $C_5$ oligosaccharides without producing unwanted degradation products. Methods for reducing $C_5$ monosaccharides degradation products produced from lignocellulosic biomass are also disclosed. In addition, compositions and products produced by the methods are disclosed.

73 Claims, 1 Drawing Sheet

(56) References Cited

OTHER PUBLICATIONS

Ballesteros et al., "Fractionation of *Cynara cardunculus* (cardoon) biomass by dilute-acid pretreatment", Appl Biochem Biotechnol. Apr. 2007;137-140(1-12):239-52., Apr. 2007, 239-52.

Bobleter, "Hydrothermal Degradation and Fractionation of Saccharides and Polysaccharides", Polysaccharides, Structural Diversity and Functional Versatility, Second Edition, Chapter 40, 1998.

Bustos et al., "Modeling of the hydrolysis of sugar cane bagasse with hydrochloric acid", Applied Biochemistry and Biotechnology, 104(1), 2003, 51-68.

Carrasco et al., "(Abstract) SO2-catalyzed steam pretreatment and fermentation of enzymatically hydrolyzed sugarcane bagasse", Enzyme and Microbial Technology, 46(2), 2010, 64-73.

Carrasco et al., "(Abstract) Effects of dilute acid and steam explosion pretreatments on the cellulose structure and kinetics of cellulosic fraction hydrolysis by dilute acids in lignocellulosic materials", Applied Biochemistry and Biotechnology, 45-46, 1994, 23-34.

Carvalho et al., "(Abstract) Sugarcane bagasse hydrolysis with phosphoric and sulfuric acids and hydrolysate detoxification for xylitol production", Journal of Chemical Technology and Biotechnology, 79(11), 2004, 1308-1312.

Chen et al., "(Abstract) Study on dilute-acid pretreatment of corn stalk", Linchan Huaxue Yu Gongye, 29(2), 2009, 27-32.

Converti et al., "(Abstract) Wood hydrolysis and hydrolyzate detoxification for subsequent xylitol production", Chemical Engineering & Technology, 23(11), 2000, 1013-1020.

Do Egito De Paiva et al., "Optimization of D-xylose, L-arabinose and D-glucose production obtained from sugar cane bagasse hydrolysis process", Brazilian Symposium on the Chemistry of Lignins and Other Wood Components, 6th, 2001, 333-7.

Dogaris et al., "Hydrothermal processing and enzymatic hydrolysis of sorghum bagasse for fermentable carbohydrates production", Bioresource Technology, 100(24), 2009, 6543-9.

Garrote et al., "(Abstract) Manufacture of xylose-based fermentation media from corncobs by posthydrolysis of autohydrolysis liquors", Applied Biochemistry and Biotechnology, 95(3), 2001, 195-207.

Geddes et al., "(Abstract) Optimizing the saccharification of sugar cane bagasse using dilute phosphoric acid followed by fungal celluloses", Bioresource Technology, 101(6), 2010, 1851-1857.

Harmer et al., "(Abstract) A new route to high yield sugars from biomass: phosphoric-sulfuric acid", Chemical Communications, vol. 43, 2009, 6610-6612.

Herrera et al., "(Abstract) Production of Xylose from Sorghum Straw Using Hydrochloric Acid", Journal of Cereal Science, vol. 37, No. 3, 2003, pp. 267-274.

Jeong et al., "(Abstract) Optimizing dilute-acid pretreatment of rapeseed straw for extraction of hemicellulose", Applied Biochemistry and Biotechnology, 161(1-8), 2010, 22-33.

Karimi et al., "Conversion of rice straw to sugars by dilute-acid hydrolysis", Biomass and Bioenergy, 30(3), 2006, 247-53.

Li et al., "(Abstract) Studies of Monosaccharide Production through Lignocellulosic Waste Hydrolysis Using Double Acids", Energy & Fuelds, 22(3), 2008, 2015-2021.

Lloyd et al., "(Abstract) Combined sugar yields for dilute sulfuric acid pretreatment of corn stover followed by enzymatic hydrolysis of the remaining solids", Bioresource Technology, 96(18), 2005, 1967-1977.

Lopez et al., "(Abstract) Chemical characterization and dilute-acid hydrolysis of rice hulls from an artisan mill", BioResources, 5(4), 2010, 2268-2277.

Lu et al., "(Abstract) Optimization of H2SO4-catalyzed hydrothermal pretreatment of rapeseed straw for bioconversion to ethanol: focusing on pretreatment at high solids content", Bioresource Technology, 100(12), 2009, 3048-3053.

McWilliams et al., "Comparison of aspen wood hydrolysates produced by pretreatment with liquid hot water and carbonic acid", Applied Biochemistry and Biotechnology, 98-100, 2002, 109-21.

Neureiter et al., "(Abstract) Dilute acid hydrolysis of presscakes from silage and grass to recover hemicellulose-derived sugars", Bioresource Technology, 92(1), 2004, 21-29.

Neureiter et al., "(Abstract) Dilute-acid hydrolysis of sugarcane bagasse at varying conditions", Applied Biochemistry and Biotechnology, 98-100, 2002, 49-58.

Overend et al., "Fractionation of Lignocellulosics by Steam-Aqueous Pretreatments", Phil. Trans. R. Soc. Lond. A 321, 1987, 523-536.

Parajo et al., "(Abstract) Pre-hydrolysis of Eucalyptus wood with dilute sulfuric acid: operation in autoclave", Holz als Roh- und Werkstoff, 52(2), 1994, 102-8.

Pessoa, Jr. et al., "(Abstract) Acid hydrolysis of hemicellulose from sugarcane bagasse", Brazilian Journal of Chemical Engineering, 14(3), 1997, 291-297.

Ramirez et al., "(Abstract) Mathematical modelling of feed pretreatment for bioethanol production", Computer-Aided Chemical Engineering, vol. 26, 2009, 1299-1304.

Roberto et al., "(Abstract) Dilute-acid hydrolysis for optimization of xylose recovery from rice straw in a semi-pilot reactor", Industrial Crops and Products, 17(3), 2003, 171-176.

Sanchez et al., "Dilute-acid hydrolysis for fermentation of the Bolivian straw material Paja Brava", Bioresource Technology, 93(3), 2004, 249-56.

Sarrouh et al., "Biotechnological production of xylitol: enhancement of monosaccharide production by post-hydrolysis of dilute acid sugarcane hydrolysate", Appl Biochem Biotechnol. May 2009;153(1-3), May 2009, 163-70.

Saucedo-Luna et al., "Optimization of acid hydrolysis of bagasse from *Agave tequilana* Weber", Revista Mexicana de Ingenieria Quimica, 9(1), 2010, 91-7.

Springer, "(Abstract) Prehydrolysis of hardwoods with dilute sulfuric acid", Industrial & Engineering Chemistry Product Research and Development, 24(4), 1985, 614-23.

Trickett et al., "(Abstract) Dilute acid hydrolysis of bagasse hemicellulose", ChemSA, 8(3), 1982, 11-15.

Um et al., "Acid Hydrolysis of Hemicellulose in Green Liquor Pre-Pulping Extract of Mixed Northern Hardwoods", Appl. Biochem Biotechnol,153(1-3), 2009, 127-38.

Van Walsum et al., "Carbonic acid enhancement of hydrolysis in aqueous pretreatment of corn stover", Bioresource Technology, 93(3), 2004, 217-226.

Van Walsum, "Severity function describing the hydrolysis of xylan using carbonic acid", Applied Biochemistry and Biotechnology, 91-93, 2001, 317-29.

Varga et al., "Optimization of steam pretreatment of corn stover to enhance enzymatic digestibility", Applied Biochemistry and Biotechnology, 113-116, 2004, 509-23.

Yee et al., "Improvement of xylose production by acid hydrolysis of bagasse pith with low liquor ratio", Report of the Taiwan Sugar Research Institute, Dec. 1982. (98), 1982, 59-70.

Zhuang et al., "Research on biomass hydrolysis under extremely low acids by HPLC", Taiyangneng Xuebao, 28(11), 2007, 1239-43.

International PCT Application No. PCT/US2012/036605, "International Search Report and Written Opinion Received", Nov. 30, 2012, 14 pages.

U.S. Appl. No. 13/464,317, "Non Final Office Action" mailed May 24, 2013 (23 pages).

International Patent Application No. PCT/US2012/036597, "International Search Report and Written Opinion" mailed Nov. 30, 2012 (10 pages).

Strobel et al., "Carbohydrate Transport by the Anaerobic Thermophile *Clostridium thermocellum* LQRI", Applied and Environmental Microbiology, 1995, 4012-4015, vol. 61, No. 11.

Yu et al., "Characteristics and Precipitation of Glucose Oligomers in the Fresh Liquid Products Obtained from the Hydrolysis of Cellulose in Hot-Compressed Water", Ind. Eng. Chem. Res., 2009, 48 (23), pp. 10682-10690, 2009, 10682-90.

Zhang et al., "Cellulose utilization by *Clostridium thermocellum*: Bioenergetics and hydrolysis product assimilation", PNAS, May 17, 2005, 7321-7325, vol. 102, No. 20.

* cited by examiner

MULTISTAGE FRACTIONATION PROCESS FOR RECALCITRANT $C_5$ OLIGOSACCHARIDES

CROSS REFERENCE TO RELATED APPLICATIONS

This application claims benefit of U.S. Application No. 61/482,400 filed May 4, 2011, the entire disclosure of which is incorporated herein by reference.

FIELD OF THE INVENTION

The present invention generally relates to methods of increasing the yields of fermentable $C_5$ sugars from lignocellulosic biomass. More particularly, it relates to methods of increasing the yields of fermentable $C_5$ sugars from lignocellulosic biomass using steps that maximize monomer formation and minimize the formation of degradation products.

BACKGROUND OF THE INVENTION

There exist methods for converting lignocellulosic biomass into fermentable $C_5$ and $C_6$ sugars. Several of these methods first produce oligomers of the $C_5$ and $C_6$ sugars, which are then hydrolyzed to form fermentable streams of monomers of $C_5$ and $C_6$ sugars. Problems exist with current methods, including, inter alia, that a certain portion of the $C_5$ oligomers is lost and not converted into $C_5$ monomer under the processing conditions. To counter this problem, the methods may be performed to drive the hydrolysis of the biomass towards monomer. However, these more stringent conditions often lead to degradation products, such as acids that inhibit fermentation. It would, therefore, be beneficial to develop methods that avoid this tradeoff to maximize monomer formation and to minimize the formation of degradation products.

Others have attempted to circumvent the problems above. For example, U.S. Pat. No. 5,125,977 is directed to a two-stage dilute acid prehydrolysis process on xylan containing hemicellulose in biomass is effected by: treating feedstock of hemicellulosic material comprising xylan that is slow hydrolyzable and xylan that is fast hydrolyzable under predetermined low temperature conditions of 90-180° C. under ambient pressure with a dilute acid for a residence time sufficient to hydrolyze the fast hydrolyzable xylan to xylose; removing said xylose from said fast hydrolyzable xylan and leaving a residue; and treating said residue having a slow hydrolyzable xylan with a dilute acid under predetermined high temperature conditions of 160-220° C. under ambient pressure for a residence time required to hydrolyze said slow hydrolyzable xylan to xylose. However, applicants are concerned with degradation products produced under much higher temperatures and pressure conditions, which causes more significant issues with control of the process, especially since the residence times are very short, relative to those typically used (7-9 minutes and 3-5 minutes, respectively, in the first and second stages of U.S. Pat. No. 5,125,977). Unexpectedly, applicants have learned how to control processes employing hot compressed water at much high temperatures used in conventional methods and at very short residence times relative to conventional methods to achieve a balance of improving the xylose yield without producing undesirable degradation products. The methods and compositions of the present invention are directed toward these, as well as other, important ends.

SUMMARY OF THE INVENTION

In one embodiment, the invention is directed to methods of increasing the level of $C_5$ monosaccharides produced from lignocellulosic biomass, comprising:
  providing a fractionated lignocellulosic biomass at a first temperature and a first pressure, wherein said fractionated lignocellulosic biomass comprises:
    a first solid fraction comprising:
      cellulose;
      lignin; and
      hemicellulose; and
    a first liquid fraction comprising:
      a soluble $C_5$ saccharide selected from the group consisting of $C_5$ oligosaccharides, xylose, arabinose, and mixtures thereof;
  separating said first solid fraction from said first liquid fraction;
  forming a slurry comprising said first solid fraction and water;
  fractionating said slurry at a second temperature and a second pressure to form:
    a second solid fraction comprising:
      cellulose; and
      lignin; and
    a second liquid fraction, comprising:
      a soluble $C_5$ saccharide selected from the group consisting of $C_5$ oligosaccharides, xylose, arabinose, and mixtures thereof;
    wherein said second temperature is greater than said first temperature;
  optionally, separating said second solid fraction from said second liquid fraction;
  optionally, combining said first liquid fraction and said second liquid fraction to form a third liquid fraction; and
  optionally, hydrolyzing said second liquid fraction or third liquid fraction at a third temperature and a third pressure to form $C_5$ saccharides selected from the group consisting of $C_5$ oligosaccharides having fewer mer units, xylose, arabinose, lyxose, ribose, and mixtures thereof.

In another embodiment, the invention is directed to methods of reducing $C_5$ monosaccharides degradation products produced from lignocellulosic biomass, comprising:
  providing a fractionated lignocellulosic biomass at a first temperature and a first pressure, wherein said fractionated lignocellulosic biomass comprises:
    a first solid fraction comprising:
      cellulose;
      lignin; and
      hemicellulose; and
    a first liquid fraction comprising:
      a soluble $C_5$ saccharide selected from the group consisting of $C_5$ oligosaccharides, xylose, arabinose, and mixtures thereof;
  separating said first solid fraction from said first liquid fraction;
  forming a slurry comprising said first solid fraction and water;
  fractionating said slurry at a second temperature and a second pressure to form:
    a second solid fraction comprising:
      cellulose; and
      lignin; and
    a second liquid fraction, comprising:
      a soluble $C_5$ saccharide selected from the group consisting of $C_5$ oligosaccharides, xylose, arabinose, and mixtures thereof;

wherein said second temperature is greater than said first temperature;
optionally, separating said second solid fraction from said second liquid fraction;
optionally, combining said first liquid fraction and said second liquid fraction to form a third liquid fraction; and
optionally, hydrolyzing said second liquid fraction or third liquid fraction at a third temperature and a third pressure to form $C_5$ saccharides selected from the group consisting of $C_5$ oligosaccharides having fewer mer units, xylose, arabinose, lyxose, ribose, and mixtures thereof.

In yet another embodiment, the invention is directed to methods of increasing the level of fermentative product or catalytic product produced from lignocellulosic biomass, comprising:
providing a fractionated lignocellulosic biomass at a first temperature and a first pressure, wherein said fractionated lignocellulosic biomass comprises:
a first solid fraction comprising:
cellulose;
lignin; and
hemicellulose; and
a first liquid fraction comprising:
a soluble $C_5$ saccharide selected from the group consisting of $C_5$ oligosaccharides, xylose, arabinose, and mixtures thereof;
separating said first solid fraction from said first liquid fraction;
forming a slurry comprising said first solid fraction and water;
fractionating said slurry at a second temperature and a second pressure to form:
a second solid fraction comprising:
cellulose; and
lignin; and
a second liquid fraction, comprising:
a soluble $C_5$ saccharide selected from the group consisting of $C_5$ oligosaccharides, xylose, arabinose, and mixtures thereof;
wherein said second temperature is greater than said first temperature; separating said second solid fraction from said second liquid fraction;
optionally, combining said first liquid fraction and said second liquid fraction to form a third liquid fraction;
hydrolyzing said second liquid fraction or third liquid fraction at a third temperature and a third pressure to form $C_5$ saccharides selected from the group consisting of $C_5$ oligosaccharides having fewer mer units, xylose, arabinose, lyxose, ribose, and mixtures thereof; and
fermenting, catalyzing, or fermenting and catalyzing said $C_5$ saccharides to form said fermentative product, said catalytic product, or a combination thereof.

In yet other embodiments, the invention is directed to products produced by the methods of the invention.

In yet other embodiments, the invention is directed to compositions, comprising:
soluble $C_5$ oligosaccharides wherein said soluble $C_5$ oligosaccharides comprise about 2 to about 15 mer units, and which preferably are capable of being membrane separated;
less than about 5% by weight of furfural; and
water.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Figure 1:
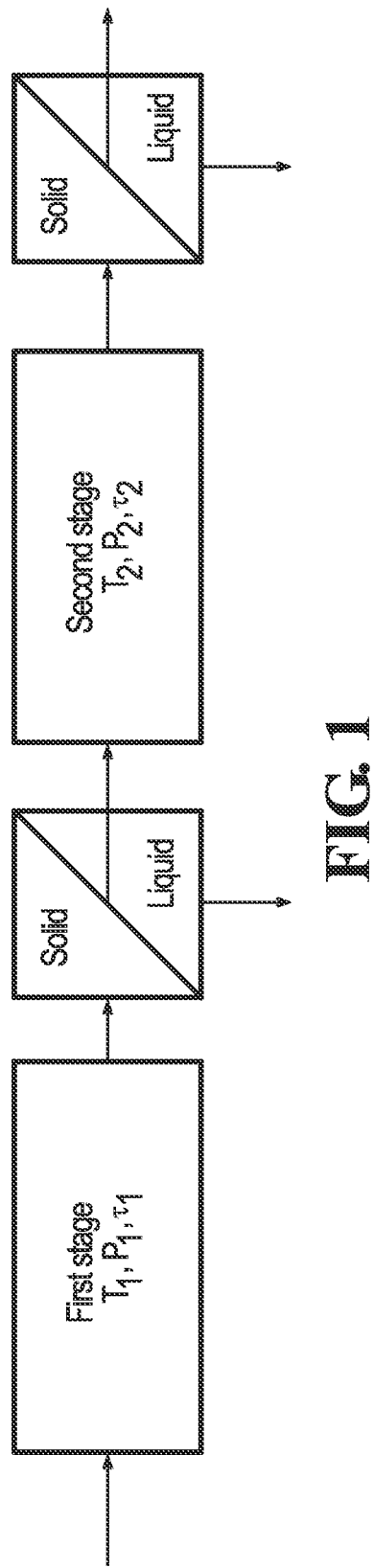
FIG. 1 is a block diagram showing the process for treating lignocellulosic biomass containing recalcitrant $C_5$ oligosaccharides.

As employed above and throughout the disclosure, the following terms, unless otherwise indicated, shall be understood to have the following meanings.

As used herein, the singular forms "a," "an," and "the" include the plural reference unless the context clearly indicates otherwise.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

A supercritical fluid is a fluid at a temperature above its critical temperature and at a pressure above its critical pressure. A supercritical fluid exists at or above its "critical point," the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, a critical temperature of about 374.2° C., and a critical pressure of about 221 bar; for carbon dioxide, a critical temperature of about 31° C. and a critical pressure of about 72.9 atmospheres (about 1072 psig). Near-critical water has a temperature at or above about 300° C. and below the critical temperature of water (374.2° C.), and a pressure high enough to ensure that all fluid is in the liquid phase.

Sub-critical water has a temperature of less than about 300° C. and a pressure high enough to ensure that all fluid is in the liquid phase. Sub-critical water temperature may be greater than about 250° C. and less than about 300° C., and in many instances sub-critical water has a temperature between about 250° C. and about 280° C. The term "hot compressed water" is used interchangeably herein for water that is at or above its critical state, or defined herein as near-critical or sub-critical, or any other temperature above about 50° C. but less than subcritical and at pressures such that water is in a liquid state As used herein, a fluid which is "supercritical" (e.g. supercritical water, supercritical $CO_2$, etc.) indicates a fluid which would be supercritical if present in pure form under a given set of temperature and pressure conditions. For example, "supercritical water" indicates water present at a temperature of at least about 374.2° C. and a pressure of at least about 221 bar, whether the water is pure water, or present as a mixture (e.g. water and ethanol, water and $CO_2$, etc). Thus, for example, "a mixture of sub-critical water and supercritical carbon dioxide" indicates a mixture of water and carbon dioxide at a temperature and pressure above that of the critical point for carbon dioxide but below the critical point for water, regardless of whether the supercritical phase contains water and regardless of whether the water phase contains any carbon dioxide. For example, a mixture of sub-critical water and supercritical $CO_2$ may have a temperature of about 250° C. to about 280° C. and a pressure of at least about 225 bar.

As used herein, "continuous" indicates a process which is uninterrupted for its duration, or interrupted, paused or suspended only momentarily relative to the duration of the process. Treatment of biomass is "continuous" when biomass is fed into the apparatus without interruption or without a substantial interruption, or processing of said biomass is not done in a batch process.

As used herein, "resides" indicates the length of time which a given portion or bolus of material is within a reaction zone or reactor vessel. The "residence time," as used herein, including the examples and data, are reported at ambient conditions and are not necessarily actual time elapsed.

As used herein, "lignocellulosic biomass or a component part thereof" refers to plant biomass containing cellulose, hemicellulose, and lignin from a variety of sources, including, without limitation (1) agricultural residues (including corn stover and sugarcane bagasse), (2) dedicated energy crops, (3) wood residues (including sawmill and paper mill discards), and (4) municipal waste, and their constituent parts including without limitation, lignocellulose biomass itself, lignin, $C_6$ saccharides (including cellulose, cellobiose, $C_6$ oligosaccharides, $C_6$ monosaccharides, and $C_5$ saccharides (including hemicellulose, $C_5$ oligosaccharides, and $C_5$ monosaccharides).

As used herein, "slurry" refers to a suspension of any viscosity of solid particles in a liquid.

Accordingly, in one embodiment, the invention is directed to methods of increasing the level of $C_5$ monosaccharides produced from lignocellulosic biomass, comprising:
  providing a fractionated lignocellulosic biomass at a first temperature and a first pressure, wherein said fractionated lignocellulosic biomass comprises:
    a first solid fraction comprising:
      cellulose;
      lignin; and
      hemicellulose; and
    a first liquid fraction comprising:
      a soluble $C_5$ saccharide selected from the group consisting of $C_5$ oligosaccharides, xylose, arabinose, and mixtures thereof;
  separating said first solid fraction from said first liquid fraction;
  forming a slurry comprising said first solid fraction and water;
  fractionating said slurry at a second temperature and a second pressure to form:
    a second solid fraction comprising:
      cellulose; and
      lignin; and
    a second liquid fraction, comprising:
      a soluble $C_5$ saccharide selected from the group consisting of $C_5$ oligosaccharides, xylose, arabinose, and mixtures thereof;
    wherein said second temperature is greater than said first temperature;
  optionally, separating said second solid fraction from said second liquid fraction;
  optionally, combining said first liquid fraction and said second liquid fraction to form a third liquid fraction; and
  optionally, hydrolyzing said second liquid fraction or third liquid fraction at a third temperature and a third pressure to form $C_5$ saccharides selected from the group consisting of $C_5$ oligosaccharides having fewer mer units (relative to the $C_5$ oligosaccharides in the second or third liquid fractions), xylose, arabinose, lyxose, ribose, and mixtures thereof.

Figure 2:
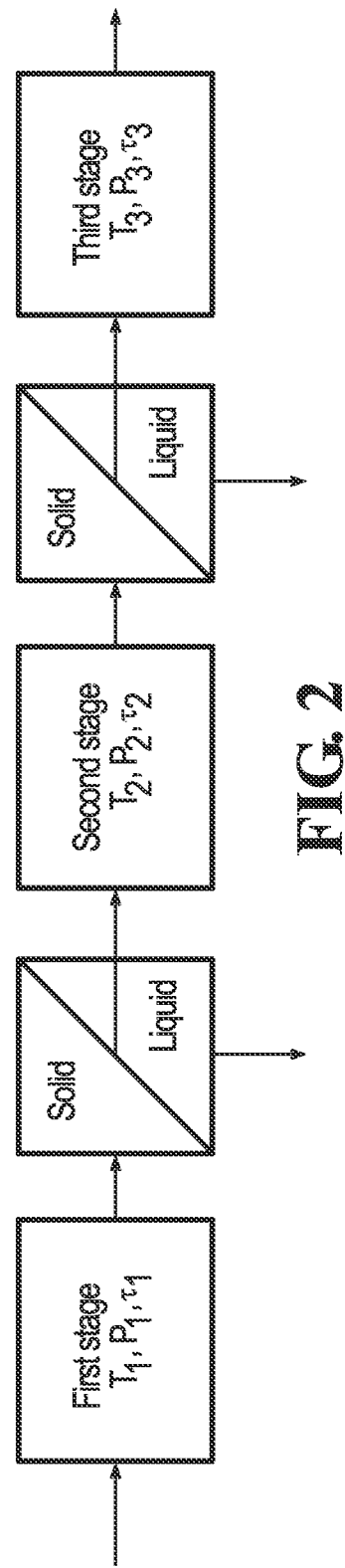
FIG. 2 is a block diagram showing the process for treating lignocellulosic biomass containing recalcitrant $C_5$ oligosaccharides and hydrolyzing to form fermentable $C_5$ saccharides.

The method is shown schematically in FIG. 1 and FIG. 2, where the first stage is the fractionation of the lignocellulosic biomass at a first temperature, pressure, and duration, the second stage is the fractionation of the slurry containing the recalcitrant, and third stage (only shown in FIG. 2) is the hydrolyzing step to form fermentable $C_5$ saccharides.

In another embodiment, the invention is directed to methods of reducing $C_5$ monosaccharides degradation products produced from lignocellulosic biomass, comprising:
  providing a fractionated lignocellulosic biomass at a first temperature and a first pressure, wherein said fractionated lignocellulosic biomass comprises:
    a first solid fraction comprising:
      cellulose;
      lignin; and
      hemicellulose; and
    a first liquid fraction comprising:
      a soluble $C_5$ saccharide selected from the group consisting of $C_5$ oligosaccharides, xylose, arabinose, and mixtures thereof;
  separating said first solid fraction from said first liquid fraction;
  forming a slurry comprising said first solid fraction and water;
  fractionating said slurry at a second temperature and a second pressure to form:
    a second solid fraction comprising:
      cellulose; and
      lignin; and
    a second liquid fraction, comprising:
      a soluble $C_5$ saccharide selected from the group consisting of $C_5$ oligosaccharides, xylose, arabinose, and mixtures thereof;
    wherein said second temperature is greater than said first temperature;
  optionally, separating said second solid fraction from said second liquid fraction;
  optionally, combining said first liquid fraction and said second liquid fraction to form a third liquid fraction; and
  optionally, hydrolyzing said second liquid fraction or third liquid fraction at a third temperature and a third pressure to form $C_5$ saccharides selected from the group consisting of $C_5$ oligosaccharides having fewer mer units (relative to the $C_5$ oligosaccharides in the second or third liquid fractions), xylose, arabinose, lyxose, ribose, and mixtures thereof.

In yet another embodiment, the invention is directed to methods of increasing the level of fermentative product or catalytic product produced from lignocellulosic biomass, comprising:

providing a fractionated lignocellulosic biomass at a first temperature and a first pressure, wherein said fractionated lignocellulosic biomass comprises:
  a first solid fraction comprising:
    cellulose;
    lignin; and
    hemicellulose; and
  a first liquid fraction comprising:
    a soluble $C_5$ saccharide selected from the group consisting of $C_5$ oligosaccharides, xylose, arabinose, and mixtures thereof;
separating said first solid fraction from said first liquid fraction;
forming a slurry comprising said first solid fraction and water;
fractionating said slurry at a second temperature and a second pressure to form:
  a second solid fraction comprising:
    cellulose; and
    lignin; and
  a second liquid fraction, comprising:
    a soluble $C_5$ saccharide selected from the group consisting of $C_5$ oligosaccharides, xylose, arabinose, and mixtures thereof;
  wherein said second temperature is greater than said first temperature;
separating said second solid fraction from said second liquid fraction;
optionally, combining said first liquid fraction and said second liquid fraction to form a third liquid fraction;
hydrolyzing said second liquid fraction or third liquid fraction at a third temperature and a third pressure to form $C_5$ saccharides selected from the group consisting of $C_5$ oligosaccharides having fewer mer units (relative to the $C_5$ oligosaccharides in the second or third liquid fractions), xylose, arabinose, lyxose, ribose, and mixtures thereof; and
fermenting, catalyzing, or fermenting and catalyzing said $C_5$ saccharides to form said fermentative product, said catalytic product, or a combination thereof.

Examples of fermentative or catalytic products include, but are not limited to, ethanol, butanol, and the like.

The conditions for the preferred temperatures and residence times at given pressures for each stage or step of the process will vary depending upon the composition of the lignocellulosic biomass to be processed, acid concentration, and the other factors and may be determined using calculating a severity factor and the combined severity factor (combining effects of acid concentration and severity). The severity factor or reaction ordinate (Ro) and combined severity factor (CS), as described by Overend, R. P; Chornet, E., *Philos. Trans. R. Soc. Lond, A*. 1987, 321, 523 and Bobleter, O., Chapter 40, *Hydrothermal Degradation and Fractionation of Saccharides and Polysaccharides*, Marcel Dekker, 2005; Um, B-H; van Walsum, G., *Appl. Biochem. Biotechnol.*, Apr. 1, 2009, all incorporated in their entirety by reference, are:

$$Ro = t \exp\frac{T-100}{14.74}$$

$$CS = \log(Ro) - pH$$

where:
t is reaction time (measured in minutes); and
T is reaction temperature (measured in ° C.).

For the determination of the actual reaction time and temperature, an experimental grid is needed to plot sugar yield as a function of Ro and/or CS to determine the maximum yield under various reaction times and reaction temperatures. Preferred temperature ranges are about 220° C. to about 240° C., where the first temperature is lower than or equal to the second temperature, which is lower than or equal to the third temperature but may be higher as the added residence time increases the severity factor. The pressure needs to be sufficient to keep the water as a liquid. Higher pressures does not influence reaction rates and, as such, should be kept as low as operationally prudent (e.g., about 5 bar above boiling) to minimize costs. Preferred residence times are about 1.0 minutes to about 5.0 minutes, more preferably about 1.5 minutes to about 3.0, and even more preferably, about 1.6 minutes to about 2.7 minutes.

In certain embodiments, the third temperature is less than the first temperature.

In certain embodiments, the lignocellulosic biomass fractionating step to process the "easy" $C_5$ oligosaccharides comprises contacting said lignocellulosic biomass with a first reaction fluid comprising hot compressed water and, optionally, carbon dioxide; wherein said first reaction fluid further comprises acid, when said lignocellulosic biomass comprises softwood; and wherein said first reaction fluid is at a temperature of at least 100° C. under a pressure sufficient to maintain said first reaction fluid in liquid form.

In certain embodiments, the step of fractionating said slurry comprising said first solid fraction and water to process the recalcitrant $C_5$ oligosaccharides comprises contacting said slurry with a second reaction fluid comprising hot compressed water and, optionally, carbon dioxide; wherein said second reaction fluid further comprises acid, when said lignocellulosic biomass comprises softwood; and wherein said second reaction fluid is at a temperature of at least 100° C. under a pressure sufficient to maintain said first reaction fluid in liquid form.

In preferred embodiments, the fractionating steps (either of the lignocellulosic biomass or the slurry comprising the first solid fraction) are carried out at a temperature no greater than about 240° C. to prevent lignin fouling of the processing equipment. In other preferred embodiments, the fractionating steps are carried out without the optional carbon dioxide. When the lignocellulosic biomass comprises hardwoods or components other than softwood, the fractionating steps are preferably carried out without the addition of acid (either inorganic or organic) or formed in situ (other than carbonic acid formed from carbon dioxide).

The hydrolysis step may be accomplished in a number of ways, including enzymatically (including using immobilized enzymes) using, for example, xylanases; by adding an aqueous acid; by contacting with a gaseous compound that forms acid in situ; and/or by contacting with a solid acid catalyst.

In certain embodiments, the hydrolyzing step comprises adding an aqueous acid to said second liquid fraction or third liquid fraction; wherein said aqueous acid is selected from the group consisting of organic acid, an inorganic acid, and combinations thereof. Suitable inorganic acid include, but are not limited to: sulfuric acid, sulfonic acid, phosphoric acid, phosphonic acid, nitric acid, nitrous acid, hydrochloric acid, hydrofluoric acid, hydrobromic acid, hydroiodic acid. Suitable organic acids include, but are not limited to, aliphatic carboxylic acids (such as acetic acid and formic acid), aromatic carboxylic acids (such as benzoic acid and salicylic acid), dicarboxylic acids (such as oxalic acid, phthalic acid, sebacic acid, and adipic acid), aliphatic fatty acids (such as oleic acid, palmitic acid, and stearic acid), aromatic fatty acids (such as phenylstearic acid), and amino acids. In certain preferred embodiments, said inorganic acid is sulfuric acid, hydrochloric acid, phosphoric acid, nitric acid, or a combination thereof. In certain particularly preferred embodiments, said inorganic acid is sulfuric acid.

In certain embodiments, the hydrolysis step to form fermentable $C_5$ saccharides comprises the use of a dilute acid. In preferred embodiments, the $C_5$ oligosaccharides are contacted with dilute acid, preferably sulfuric acid, at a level of about 0.05% to about 2%, by weight, based on the weight of the slurry biomass, for a time sufficient to hydrolyze said $C_5$ oligosaccharides to fermentable $C_5$ saccharides ($C_5$ oligosaccharides having few mer units, xylose, arabinose, or mixtures thereof). In certain other embodiments, the amount of acid may be present in an amount from about 0.07% to about 2%, about 0.1% to about 1.5%, about 0.1% to about 1%, about 0.1% to about 0.5%, about 0.1% to about 0.4%, about 0.1% to about 0.3%, about 0.1% to about 0.2%, about 0.5% to about 2%, about 0.5% to about 1.5%, about 0.5% to about 1%, less than about 2%, less than about 1.5%, less than about 1%, less than about 0.5%, less than about 0.4%, less than about 0.3%, less than about 0.2%, or less than about 0.1%.

In certain embodiments, the hydrolyzing step comprises contacting said second liquid fraction or third liquid fraction with a gaseous compound that forms acid in situ. Suitable gaseous compounds that form acid in situ include, but are not limited to, $SO_2$, $CO_2$, $NO_2$, HX (where X is Cl, Br, F, or I), or a combination thereof. In certain embodiments, the acid is present at a level of about 0.05%, by weight, to about 2.0%, by weight, based on the total weight of liquid fraction. In certain other embodiments, the amount of acid may be present in an amount from about 0.07% to about 2%, about 0.1% to about 1.5%, about 0.1% to about 1%, about 0.1% to about 0.5%, about 0.1% to about 0.4%, about 0.1% to about 0.3%, about 0.1% to about 0.2%, about 0.5% to about 2%, about 0.5% to about 1.5%, about 0.5% to about 1%, less than about 2%, less than about 1.5%, less than about 1%, less than about 0.5%, less than about 0.4%, less than about 0.3%, less than about 0.2%, or less than about 0.1%.

In yet other embodiments, the hydrolysis step comprises contacting said second liquid fraction or third liquid fraction with a solid acid catalyst. Suitable solid acid catalysts include, but are not limited to, zeolites, cation exchange resins, or combinations thereof.

In certain embodiments, the soluble $C_5$ oligosaccharides in said first liquid fraction comprise about 2 to about 15 mer units, and preferably are capable of being membrane separated. In certain embodiments, the soluble $C_5$ oligosaccharides in said second liquid fraction comprise about 2 to about 15 mer units.

Preferably, the yield of said $C_5$ monosaccharides is at least 60% of theoretical yield. Preferably, the yield of said xylose is at least 60% of theoretical yield.

In certain embodiments, the methods further comprise the step of converting said soluble $C_5$ saccharides into at least one of said acetic acid and furfural by conventional methods well known to those in the art, including, for example, dehydration with an inorganic acid (such as sulfuric acid at pH 1-2) at elevated temperatures (e.g., greater than about 240° C. to about 300° C.) for about 10 seconds.

In certain embodiments of the methods, said first temperature is of at least about 210° C., preferably, at least about 220° C., and more preferably, at least about 225° C.

In certain embodiments of the methods, said second temperature is of at least about 220° C., preferably, at least about 225° C., and more preferably, at least about 235° C.

In certain embodiments of the methods, said lignocellulosic biomass is derived from hardwood.

In certain embodiments, said method is conducted substantially free of exogenous acid.

The methods of the invention are preferably run continuously, although they may be run as batch or semi-batch processes.

The methods of the invention may be carried out in any suitable reactor, including, but not limited to, a tubular reactor, a digester (vertical, horizontal, or inclined), or the like. Suitable digesters include the digester system described in U.S. Pat. No. 8,057,639, which include a digester and a steam explosion unit, the entire disclosure of which is incorporated by reference.

In certain embodiments, the $C_5$ saccharides ($C_5$ oligosaccharides xylose, arabinose, lyxose, ribose, or mixtures thereof) are fermented to ethanol, butanol, and mixtures thereof, using techniques known to those skilled in the art, including, but not limited to, yeast fermentations using *Saccharomyces cerevisiae* and *Clostridium* sp. In certain preferred embodiments, an oligomer fermentor is able to uptake oligomers directly (generally up to a maximum size, for example, of 6 mer units, for *Clostridium thermocellum*).

In certain embodiments, the invention is directed to the products produced by the methods of the invention. Furfural and formic acid are major degradation products in the dehydration route. Glycolaldehyde, glyceraldehyde, dihydroxyacetone, and pyruvaldehyde, which are products produced via retro-aldol route, are also other possible degradation products. Preferably, the yield of degradation products is no greater than about 15% of theoretical yield.

In yet other embodiments, the invention is directed to compositions, comprising:
  soluble $C_5$ oligosaccharides;
  wherein said soluble $C_5$ oligosaccharides have about 2 to about 15 mer units;
  less than about 5% by weight of furfural; and
  water.

In certain embodiments, the compositions comprise $C_5$ oligosaccharides having about 2 mer units to about 15 mer units; and water. In certain preferred embodiments, the compositions have a pH of about 1.5 to about 3.0, preferably about 2.0 to about 2.5.

The products produced by the methods of the invention may be utilized in a wide variety of applications, where C5 sugars are conventionally utilized, including, but not limited to, the production of various chemicals and fuels using fermentative, enzymatic, catalytic, and non-catalytic (e.g., thermal decomposition) processes. Such processes are useful for preparing feedstocks for the preparation of the following non-exhaustive list:
  fuels (such as gasoline, jet fuel, butanol, and the like);
  chemicals (such as acetic acid, acetic anhydride, acetone, acrylic acid, adipic acid, benzene, ethanol, ethylene, ethylene glycol, ethylene oxide, methanol, polypropylene, terephthalic acid, toluene, xylene, 1,3-propanediol, 1,4-butanediol, and the like);

pharmaceuticals and foods (such as acetoin, alanine, arabitol, ascorbic acid, aspartic acid, citric acid, coumaric acid, fumaric acid, glycerol, glycine, kojic acid, lactic acid, lysine, malonic acid, proline, propionic acid, serine, sorbitol, succinic acid, threonine, xylitol, sugar acids (glucaric acid, gluconic acid, xylonic acids), and the like);

specialty chemicals (such as acontic acid, glutamic acid, malic acid, oxalic acid, and the like);

textile applications (such as formic acid and the like); and industrial intermediates (acetaldehyde, 3-hydroxypropionic acid, 2,5-furan dicarboxylic acid, furfural, glutaric acid, itaconic acid, levulinic acid, and the like).

While the preferred forms of the invention have been disclosed, it will be apparent to those skilled in the art that various changes and modifications may be made that will achieve some of the advantages of the invention without departing from the spirit and scope of the invention. Therefore, the scope of the invention is to be determined solely by the claims to be appended.

When ranges are used herein for physical properties, such as molecular weight, or chemical properties, such as chemical formulae, all combinations, and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of producing $C_5$ monosaccharides from lignocellulosic biomass, comprising:
    providing a fractionated lignocellulosic biomass at a first temperature of at least about 200° C. and a first pressure, wherein said fractionated lignocellulosic biomass comprises:
        a first solid fraction comprising:
            cellulose;
            lignin; and
            hemicellulose; and
        a first liquid fraction comprising:
            a soluble $C_5$ saccharide selected from the group consisting of $C_5$ oligosaccharides, xylose, arabinose, and mixtures thereof;
    separating said first solid fraction from said first liquid fraction;
    forming a slurry comprising said first solid fraction and water;
    fractionating said slurry at a second temperature of at least about 200° C. and a second pressure to form:
        a second solid fraction comprising:
            cellulose; and
            lignin; and
        a second liquid fraction, comprising:
            a soluble $C_5$ saccharide selected from the group consisting of $C_5$ oligosaccharides, xylose, arabinose, and mixtures thereof;
        wherein said second temperature is greater than said first temperature;
    optionally, separating said second solid fraction from said second liquid fraction;
    optionally, combining said first liquid fraction and said second liquid fraction to form a third liquid fraction; and
    optionally, hydrolyzing said second liquid fraction or third liquid fraction at a third temperature and a third pressure to form $C_5$ saccharides selected from the group consisting of $C_5$ oligosaccharides having fewer mer units, xylose, arabinose, lyxose, ribose, and mixtures thereof;
    wherein said fractionating said slurry is conducted substantially free of added acid.

2. A method of claim 1,
wherein said first temperature is of at least about 210° C.

3. A method of claim 1,
wherein said first temperature is of at least about 220° C.

4. A method of claim 1,
wherein said first temperature is of at least about 225° C.

5. A method of claim 1,
wherein said second temperature is of at least about 220° C.

6. A method of claim 1,
wherein said second temperature is of at least about 225° C.

7. A method of claim 1,
wherein said second temperature is of at least about 235° C.

8. A method of claim 1,
wherein said lignocellulosic biomass is derived from hardwood.

9. A method of claim 1,
wherein said fractionating said slurry is conducted free of added acid.

10. A method of claim 1,
wherein said method is continuous.

11. A method of claim 1,
wherein said third temperature is less than said first temperature.

12. A method of claim 1,
wherein said first pressure and second pressure are greater than atmospheric pressure.

13. A method of claim 1,
wherein said fractionated lignocellulosic biomass is prepared by contacting said lignocellulosic biomass with a first reaction fluid comprising hot compressed water and, optionally, carbon dioxide;
wherein said first reaction fluid further comprises acid, when said lignocellulosic biomass comprises softwood; and
wherein said first reaction fluid is at a temperature of at least 100° C. under a pressure sufficient to maintain said first reaction fluid in liquid form.

14. A method of claim 1,
wherein as a part of said fractionating said slurry is contacted with a second reaction fluid comprising hot compressed water; and
wherein said second reaction fluid is at a temperature of at least 100° C. under a pressure sufficient to maintain said second reaction fluid in liquid form.

15. A method of claim 1,
wherein said hydrolyzing is performed and comprises adding an aqueous acid to said second liquid fraction or third liquid fraction;
wherein said aqueous acid is selected from the group consisting of organic acid, an inorganic acid, and combinations thereof.

16. A method of claim 15,
wherein said inorganic acid is sulfuric acid, hydrochloric acid, phosphoric acid, nitric acid, or a combination thereof.

17. A method of claim 16,
wherein said inorganic acid is sulfuric acid.

18. A method of claim 1,
wherein said hydrolyzing is performed and comprises contacting said second liquid fraction or third liquid fraction with a gaseous compound that forms acid in situ.

19. A method of claim 18,
wherein said gaseous compound is $SO_2$, $CO_2$, $NO_2$, HX (where X is Cl, Br, F, or I), or a combination thereof.

20. A method of claim 1,
wherein said hydrolyzing is performed and comprises contacting said second liquid fraction or third liquid fraction with a solid acid catalyst.

21. A method of claim 20,
wherein said solid acid catalyst is a zeolite, a cation exchange resin, or a combination thereof.

22. A method of claim 1,
wherein said hydrolyzing is performed and comprises contacting said second liquid fraction or third liquid fraction with at least one immobilized enzyme.

23. A method of claim 1,
wherein said soluble $C_5$ oligosaccharides in said first liquid fraction comprise about 2 mer units to about 15 mer units.

24. A method of claim 1,
wherein said soluble $C_5$ oligosaccharides in said second liquid fraction comprise about 2 mer units to about 15 mer units.

25. A method of claim 1, further comprising:
producing at least one of acetic acid and furfural from said soluble $C_5$ saccharides.

26. A method of claim 1,
wherein the yield of said $C_5$ monosaccharides is at least 60% of theoretical yield.

27. A method of claim 1,
wherein the yield of said xylose is at least 60% of theoretical yield.

28. A method of claim 1,
wherein said method is conducted substantially free of added acid.

29. A method of claim 1,
wherein said method is conducted free of added acid.

30. A method of claim 1,
wherein said separating said second solid fraction from said second liquid fraction is performed.

31. A method of producing $C_5$ monosaccharides from lignocellulosic biomass, comprising:
providing a fractionated lignocellulosic biomass at a first temperature and a first pressure, wherein said fractionated lignocellulosic biomass comprises:
a first solid fraction comprising:
cellulose;
lignin; and
hemicellulose; and
a first liquid fraction comprising:
a soluble $C_5$ saccharide selected from the group consisting of $C_5$ oligosaccharides, xylose, arabinose, and mixtures thereof;
separating said first solid fraction from said first liquid fraction;
forming a slurry comprising said first solid fraction and water;
fractionating said slurry at a second temperature and a second pressure to form:
a second solid fraction comprising:
cellulose; and
lignin; and
a second liquid fraction, comprising:
a soluble $C_5$ saccharide selected from the group consisting of $C_5$ oligosaccharides, xylose, arabinose, and mixtures thereof;
wherein said second temperature is greater than said first temperature;
optionally, separating said second solid fraction from said second liquid fraction;
optionally, combining said first liquid fraction and said second liquid fraction to form a third liquid fraction; and
optionally, hydrolyzing said second liquid fraction or third liquid fraction at a third temperature and a third pressure to form $C_5$ saccharides selected from the group consisting of $C_5$ oligosaccharides having fewer mer units, xylose, arabinose, lyxose, ribose, and mixtures thereof;
wherein said fractionating said slurry is conducted substantially free of added acid.

32. A method of claim 31,
wherein said method is continuous.

33. A method of claim 31,
wherein said third temperature is less than said first temperature.

34. A method of claim 31,
wherein said first pressure and second pressure are greater than atmospheric pressure.

35. A method of claim 31,
wherein said fractionated lignocellulosic biomass is formed by contacting said lignocellulosic biomass with a first reaction fluid comprising hot compressed water and, optionally, carbon dioxide;
wherein said first reaction fluid further comprises acid, when said lignocellulosic biomass comprises softwood;
wherein said first reaction fluid is at a temperature of at least 100° C. under a pressure sufficient to maintain said first reaction fluid in liquid form.

36. A method of claim 31,
wherein said fractionating said slurry comprises contacting said slurry with a second reaction fluid comprising hot compressed water; and
wherein said second reaction fluid is at a temperature of at least 100° C. under a pressure sufficient to maintain said first reaction fluid in liquid form.

37. A method of claim 31,
wherein said hydrolyzing is performed and comprises adding an aqueous acid to said second liquid fraction or third liquid fraction;
wherein said aqueous acid is selected from the group consisting of organic acid, an inorganic acid, and combinations thereof.

38. A method of claim 37,
wherein said inorganic acid is sulfuric acid, hydrochloric acid, phosphoric acid, nitric acid, or a combination thereof.

39. A method of claim 38,
wherein said inorganic acid is sulfuric acid.

40. A method of claim 31,
wherein said hydrolyzing is performed and comprises contacting said second liquid fraction or third liquid fraction with a gaseous compound that forms acid in situ.

41. A method of claim 40,
wherein said gaseous compound is $SO_2$, $CO_2$, $NO_2$, HX (where X is Cl, Br, F, or I), or a combination thereof.

42. A method of claim 31,
wherein said hydrolyzing is performed and comprises contacting said second liquid fraction or third liquid fraction with a solid acid catalyst.

43. A method of claim 42,
wherein said solid acid catalyst is a zeolite, a cation exchange resin, or a combination thereof.

44. A method of claim 31,
wherein said hydrolyzing is performed and comprises contacting said second liquid fraction or third liquid fraction with at least one immobilized enzyme.

45. A method of claim 31,
wherein said soluble $C_5$ oligosaccharides in said first liquid fraction comprise about 2 mer units to about 15 mer units.

46. A method of claim 31,
wherein said soluble $C_5$ oligosaccharides in said second liquid fraction comprise about 2 mer units to about 15 mer units.

47. A method of claim 31,
wherein said method produces $C_5$ monosaccharides degradation products, and said $C_5$ monosaccharides degradation products are compounds selected from the group consisting of furfural, formic acid, glycolaldehyde, glyceraldehyde, dihydroxyacetone, pyruvaldehyde, and combinations thereof.

48. A method of claim 47,
wherein the yield of said degradation products is no greater than about 15% of theoretical yield.

49. A method of claim 31,
wherein the yield of said $C_5$ monosaccharides is at least about 60% of theoretical yield.

50. A method of claim 31,
wherein the yield of said xylose is at least about 60% of theoretical yield.

51. A method of claim 31,
wherein said method is conducted substantially free of added acid.

52. A method of claim 31,
wherein said method is conducted free of added acid.

53. A method of claim 31,
wherein said fractionating said slurry is conducted free of added acid.

54. A method of claim 31,
wherein said separating said second solid fraction from said second liquid fraction is performed.

55. A method of claim 31,
wherein said combining said first liquid fraction and said second liquid fraction to form a third liquid fraction is performed.

56. A method comprising:
providing a fractionated lignocellulosic biomass at a first temperature and a first pressure, wherein said fractionated lignocellulosic biomass comprises:
a first solid fraction comprising:
cellulose;
lignin; and
hemicellulose; and
a first liquid fraction comprising:
a soluble $C_5$ saccharide selected from the group consisting of $C_5$ oligosaccharides, xylose, arabinose, and mixtures thereof;
separating said first solid fraction from said first liquid fraction;
forming a slurry comprising said first solid fraction and water;
fractionating said slurry at a second temperature and a second pressure to form:
a second solid fraction comprising:
cellulose; and
lignin; and
a second liquid fraction, comprising:
a soluble $C_5$ saccharide selected from the group consisting of $C_5$ oligosaccharides, xylose, arabinose, and mixtures thereof;
wherein said second temperature is greater than said first temperature;
optionally, separating said second solid fraction from said second liquid fraction;
optionally, combining said first liquid fraction and said second liquid fraction to form a third liquid fraction;
optionally, hydrolyzing said second liquid fraction or third liquid fraction at a third temperature and a third pressure to form $C_5$ saccharides selected from the group consisting of $C_5$ oligosaccharides having fewer mer units, xylose, arabinose, lyxose, ribose, and mixtures thereof; and
optionally, fermenting, catalyzing, or fermenting and catalyzing said $C_5$ saccharides to form a fermentative product, a catalytic product, or a combination thereof;
wherein said method is conducted substantially free of added acid.

57. A method of claim 56,
wherein said method is continuous.

58. A method of claim 56,
wherein said third temperature is less than said first temperature.

59. A method of claim 56,
wherein said first pressure and second pressure are greater than atmospheric pressure.

60. A method of claim 56,
wherein said fractionated lignocellulosic biomass is formed by contacting lignocellulosic biomass with a first reaction fluid comprising hot compressed; and
wherein said first reaction fluid is at a temperature of at least 100° C. under a pressure sufficient to maintain said first reaction fluid in liquid form.

61. A method of claim 56,
wherein said fractionating comprises said slurry comprises contacting said slurry with a second reaction fluid comprising hot compressed water; and
wherein said second reaction fluid is at a temperature of at least 100° C. under a pressure sufficient to maintain said first reaction fluid in liquid form.

62. A method of claim 56,
wherein said hydrolyzing is performed and comprises contacting said second liquid fraction or third liquid fraction with at least one immobilized enzyme.

63. A method of claim 56,
wherein said soluble $C_5$ oligosaccharides in said first liquid fraction comprise about 2 mer units to about 15 mer units.

64. A method of claim 56,
wherein said soluble $C_5$ oligosaccharides in said second liquid fraction comprise about 2 mer units to about 15 mer units.

65. A method of claim 56,
wherein said method produces $C_5$ monosaccharides degradation products, and said $C_5$ monosaccharides degradation products are compounds selected from the group consisting of furfural, formic acid, glycolaldehyde, glyceraldehyde, dihydroxyacetone, pyruvaldehyde, and combinations thereof.

66. A method of claim 65,
wherein the yield of said degradation products is no greater than about 15% of theoretical yield.

67. A method of claim 56,
wherein said hydrolyzing is performed;

wherein said fermenting, catalyzing, or fermenting and catalyzing is performed; and wherein the yield of said fermentative product or catalytic product is at least about 60% of theoretical yield.

68. A method of claim 56, wherein the yield of said xylose is at least about 60% of theoretical yield.

69. A method of claim 56, wherein said method is conducted free of added acid.

70. A method of claim 56, wherein said first temperature is at least about 200° C.

71. A method of claim 56, wherein said second temperature is at least about 200° C.

72. A method of claim 56, wherein said separating said second solid fraction from said second liquid fraction is performed.

73. A method of claim 56, wherein said combining said first liquid fraction and said second liquid fraction to form a third liquid fraction is performed.

* * * * *